(12) United States Patent
Ito

(10) Patent No.: US 9,862,918 B2
(45) Date of Patent: Jan. 9, 2018

(54) WELL PLATE AND SUCTION DEVICE PROVIDED WITH WELL PLATE

(75) Inventor: Saburo Ito, Shizuoka-ken (JP)

(73) Assignee: YAMAHA HATSUDOKI KABUSHIKI KAISHA, Shizuoka-ken (JP)

( * ) Notice: Subject to any disclaimer, the term of this patent is extended or adjusted under 35 U.S.C. 154(b) by 585 days.

(21) Appl. No.: 14/372,202

(22) PCT Filed: Jan. 19, 2012

(86) PCT No.: PCT/JP2012/000327
§ 371 (c)(1),
(2), (4) Date: Jul. 14, 2014

(87) PCT Pub. No.: WO2013/108293
PCT Pub. Date: Jul. 25, 2013

(65) Prior Publication Data
US 2015/0072405 A1  Mar. 12, 2015

(51) Int. Cl.
*C12M 1/00* (2006.01)
*C12M 1/34* (2006.01)
(Continued)

(52) U.S. Cl.
CPC ........... *C12M 23/12* (2013.01); *B01L 3/5085* (2013.01); *B01L 3/502761* (2013.01);
(Continued)

(58) Field of Classification Search
CPC .... B01J 2219/00315; B01J 2219/00414; B01J 2219/00468; B01L 2200/0647;
(Continued)

(56) References Cited

U.S. PATENT DOCUMENTS 3,190,731 A   6/1965  Weiskopf
3,545,932 A  12/1970  Gilford et al.
(Continued)

FOREIGN PATENT DOCUMENTS

EP   0834729 A2   4/1998
EP   1722235 A1  11/2006
(Continued)

OTHER PUBLICATIONS

Communication pursuant to Rule 164(1) EPC issued by the European Patent Office dated May 18, 2015, which corresponds to European Patent Application No. 12865628.7-1361 and is related to U.S. Appl. No. 14/372,202.
(Continued)

*Primary Examiner* — Nathan Bowers
*Assistant Examiner* — Lydia Edwards
(74) *Attorney, Agent, or Firm* — Studebaker & Brackett PC

(57) ABSTRACT

A well plate is formed with a well for holding a subject to be sucked by a suction nozzle on an inner bottom part and storing liquid and, a clearance forming member for forming a clearance to allow the liquid to flow in a state where a tip part of the suction nozzle is inserted into and held in contact with the well is provided in the well. According to the present invention, the clearance enabling the liquid to flow is formed even in the state where the tip part of the suction nozzle is inserted into and held in contact with the well in sucking the subject held in the well by the suction nozzle. The suction nozzle can suck the liquid around through the clearance and the subject held in the well is efficiently sucked through the suction port along the flow of the sucked liquid.

9 Claims, 6 Drawing Sheets

(51) Int. Cl.
*C12M 3/00* (2006.01)
*C12M 1/32* (2006.01)
*B01L 3/00* (2006.01)
*G01N 35/10* (2006.01)
*B01L 3/02* (2006.01)

(52) U.S. Cl.
CPC . *G01N 35/1011* (2013.01); *B01J 2219/00315* (2013.01); *B01J 2219/00414* (2013.01); *B01J 2219/00468* (2013.01); *B01L 3/021* (2013.01); *B01L 2200/0647* (2013.01); *B01L 2200/0657* (2013.01); *B01L 2200/0668* (2013.01); *B01L 2200/0684* (2013.01); *B01L 2300/0819* (2013.01); *B01L 2300/0829* (2013.01); *B01L 2300/0858* (2013.01)

(58) Field of Classification Search
CPC ..... B01L 2200/0657; B01L 2200/0668; B01L 2200/0684; B01L 2300/0819; B01L 2300/0829; B01L 2300/0858; B01L 3/021; B01L 3/502761
USPC ....................................................... 435/288.4
See application file for complete search history.

(56) References Cited

U.S. PATENT DOCUMENTS

| | | | |
|---|---|---|---|
| 4,952,518 A | 8/1990 | Johnson et al. | |
| 4,980,293 A | 12/1990 | Jeffs | |
| 5,419,278 A | 5/1995 | Carter | |
| 5,582,796 A | 12/1996 | Carey et al. | |
| 5,637,275 A | 6/1997 | Carey et al. | |
| 5,653,940 A | 8/1997 | Carey et al. | |
| 5,679,948 A | 10/1997 | Carey et al. | |
| 5,741,708 A | 4/1998 | Carey et al. | |
| 5,795,748 A * | 8/1998 | Cottingham | B01L 3/5085 422/82.05 |
| 6,063,340 A | 5/2000 | Lewis et al. | |
| 6,074,615 A | 6/2000 | Lewis et al. | |
| 6,143,250 A | 11/2000 | Tajima | |
| 6,337,053 B1 | 1/2002 | Tajima | |
| 6,436,349 B1 | 8/2002 | Carey et al. | |
| 6,498,037 B1 | 12/2002 | Carey et al. | |
| 6,555,062 B1 | 4/2003 | Lewis et al. | |
| 6,602,474 B1 | 8/2003 | Tajima | |
| 7,993,525 B2 * | 8/2011 | Su | G01N 1/4044 210/222 |
| 2002/0085959 A1 | 7/2002 | Carey et al. | |
| 2003/0194349 A1 | 10/2003 | Carey et al. | |
| 2004/0228774 A1 | 11/2004 | Ogawa et al. | |
| 2005/0058577 A1 | 3/2005 | Micklash, II et al. | |
| 2005/0136546 A1 | 6/2005 | Berndt et al. | |
| 2005/0266570 A1 | 12/2005 | Carey et al. | |
| 2006/0013729 A1 | 1/2006 | Carey et al. | |
| 2006/0257994 A1 | 11/2006 | Noda et al. | |
| 2007/0059763 A1 | 3/2007 | Okano et al. | |
| 2007/0082390 A1 * | 4/2007 | Hastings | B01L 3/5085 435/305.2 |
| 2009/0042200 A1 | 2/2009 | Okano et al. | |
| 2009/0042739 A1 | 2/2009 | Okano et al. | |
| 2009/0325215 A1 | 12/2009 | Okano et al. | |
| 2010/0016568 A1 | 1/2010 | Okano et al. | |
| 2010/0016569 A1 | 1/2010 | Okano et al. | |
| 2010/0018862 A1 | 1/2010 | Okano et al. | |
| 2010/0021933 A1 | 1/2010 | Okano et al. | |
| 2010/0179074 A1 | 7/2010 | Milne | |
| 2013/0037059 A1 | 2/2013 | Stafford | |
| 2013/0252848 A1 | 9/2013 | Okano et al. | |
| 2014/0322747 A1 | 10/2014 | Ito | |

FOREIGN PATENT DOCUMENTS

| | | |
|---|---|---|
| EP | 2796540 A1 | 10/2014 |
| GB | 2472321 A | 2/2011 |
| JP | 40-005470 A | 3/1965 |
| JP | 50-013677 B1 | 5/1975 |
| JP | 03-081558 U | 8/1991 |
| JP | 2002-340908 A | 11/2002 |
| JP | 2004-333404 A | 11/2004 |
| JP | 2005-177749 A | 7/2005 |
| JP | 2006-115723 A | 5/2006 |
| JP | 2007-326072 A | 12/2007 |
| JP | 2009-002674 A | 1/2009 |
| JP | 2009-236838 A | 10/2009 |
| WO | 1997/005492 A1 | 2/1997 |
| WO | 2004/091746 A2 | 10/2004 |

OTHER PUBLICATIONS

The extended European search report issued by the European Patent Office dated Jul. 24, 2015, which corresponds to European Patent Application No. 12865628.7-1361 and is related to U.S. Appl. No. 14/372,202.

International Search Report; PCT/JP2012/000327; dated Mar. 13, 2012.

* cited by examiner

WELL PLATE AND SUCTION DEVICE PROVIDED WITH WELL PLATE

CROSS REFERENCE TO RELATED APPLICATIONS

This application claims benefit of priority to International Patent Application No. PCT/JP2012/000327 filed on Jan. 19, 2012, the entire content of which is incorporated herein by reference.

TECHNICAL FIELD

The present technical field relates to a well plate and a suction device provided with the well plate. More specifically, the present disclosure relates to a well plate enabling a subject to be efficiently collected without stopping the flow of liquid simultaneously sucked in sucking the subject held in a well by a suction nozzle and a suction device provided with the well plate.

BACKGROUND

Conventionally, a plate provided with wells has been used to select particles according to sizes and shapes (hereinafter, these are referred to as shapes in some cases) in various fields. A user observes the particles in a state held in the wells of the plate and selects and collects only the particles of a predetermined shape. Larger articles to be selected include tablets, capsules and granulated granules and smaller ones include bio-based cells used in the fields of bio-related technology and medicine. For example, the user can make deviations of test conditions in various tests using cells smaller by selecting the cells and making the shapes thereof uniform. The selected cells can be subjected to high-throughput screening (HTS) and the like.

There are various methods for collecting subjects held in wells. For example, a method for sucking and collecting subjects using a push-button type suction pipette provided with a suction tip or a suction nozzle on its tip is adopted in a biochemical experiment or the like. If specimens vulnerable to dryness such as cells are subjects, an operation is preferably performed in liquid to prevent the drying of the subjects. In the case of sucking the subjects in the liquid, a liquid flow is generated from a suction port into a suction path to suck the subject in the well by simultaneously sucking the liquid around the well.

However, in a state where a tip part of the suction nozzle is inserted in the well, an inner wall or an inner bottom part of the well and the tip part of the suction nozzle may be held in close contact to block a flow passage for the liquid. In this case, there is a problem of being unable to suck the subject held in the well since the liquid around the well cannot be sucked.

In view of such a problem, a container for sucking/discharging a fixed quantity without closing a suction port is disclosed in International Publication No. 97/5492. A gap portion having a narrower width than an opening of a tip part of the suction port is formed on an inner bottom part of the container of International Publication No. 97/5492. A well formed with a groove on the outer periphery is disclosed in Japanese Unexamined Patent Publication No. 2007-326072. The well of Japanese Unexamined Patent Publication No. 2007-326072 is formed with the groove having such a width that fine specimens cannot be fitted into the groove.

SUMMARY

However, the container of International Publication No. 97/5492 has a problem that the subject can be sucked if it is composed only of liquid, but subjects cannot be sucked depending on diameters thereof in the case of sucking particles or the like since the subjects are fitted into or caught by the gap portion such as a groove provided on the inner bottom part. The well of Japanese Unexamined Patent Publication No. 2007-326072 has a problem that some fine specimens cannot be sucked by being caught by the groove and clogged in the well since the groove is formed on an outer side. Particularly, if the subjects are those having a soft property such as cells, there is a problem that the subjects are deformed by forcible suction or tissues are destroyed.

The present disclosure was developed in view of such conventional problems and aims to provide a well plate enabling a subject to be efficiently collected without stopping the flow of liquid simultaneously sucked in sucking the subject held in a well by a suction nozzle and a suction device provided with the well plate.

A well plate according to one aspect of the present disclosure is a well plate used by being immersed in liquid and formed with a well for holding a subject to be sucked by a suction nozzle including a suction port on an inner bottom part, and a clearance forming member for forming a clearance to allow the liquid to flow in a state where a tip part of the suction nozzle including the suction port is inserted into and held in contact with the well is provided in the well.

A suction device according to another aspect of the present disclosure includes a container for storing liquid, a well plate to be immersed in the container and formed with a well for holding a subject on an inner bottom part, and a suction nozzle including a suction port for sucking the subject held in the well, and the well includes a clearance forming member for forming a clearance to allow the liquid to flow in a state where a tip part of the suction nozzle including the suction port is inserted into and held in contact with the well.

An object, features and advantages of the present disclosure will become more apparent upon reading the following detailed description along with the accompanying drawings.

DETAILED DESCRIPTION

First Embodiment

Figure 1:
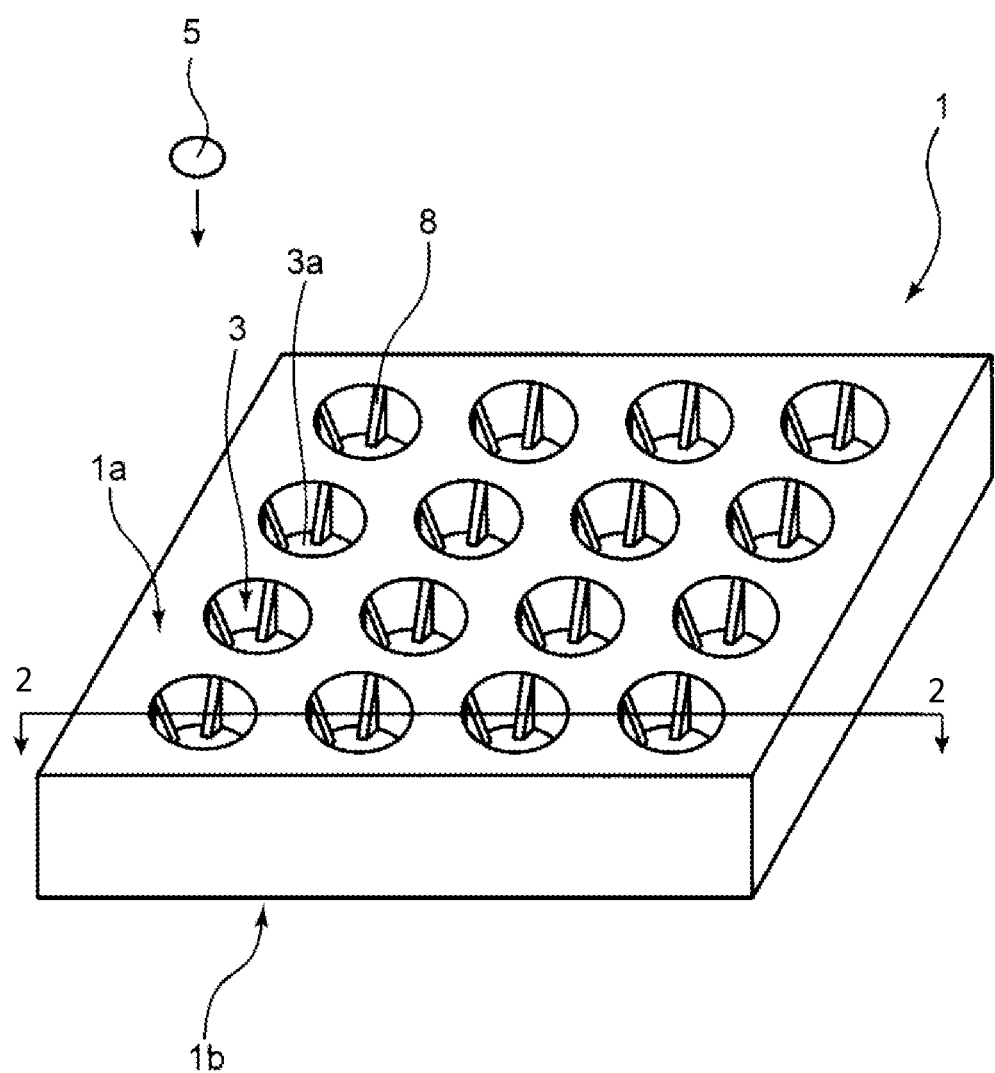
FIG. 1 is a perspective view of a well plate according to a first embodiment of the present disclosure.
Figure 2A:
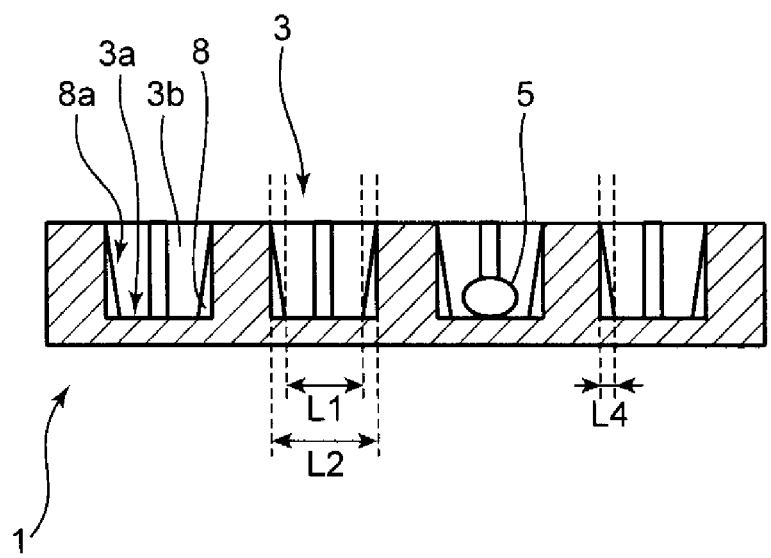
FIGS. 2A and 2B are views showing wells of the well plate according to the first embodiment of the present disclosure.
Figure 2B:
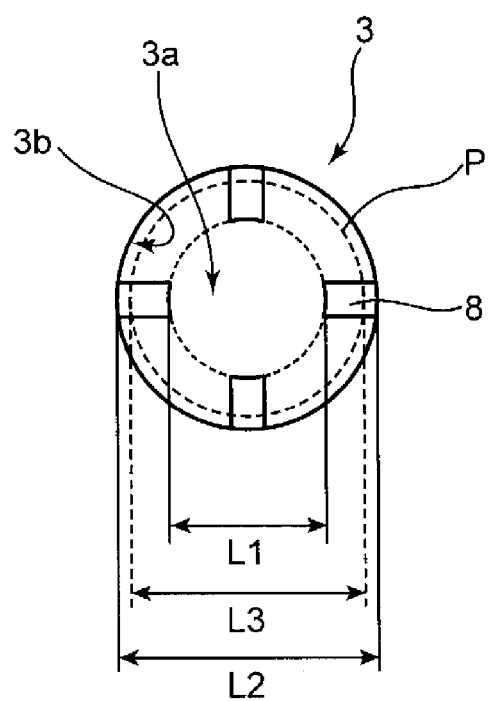
Figure 3:
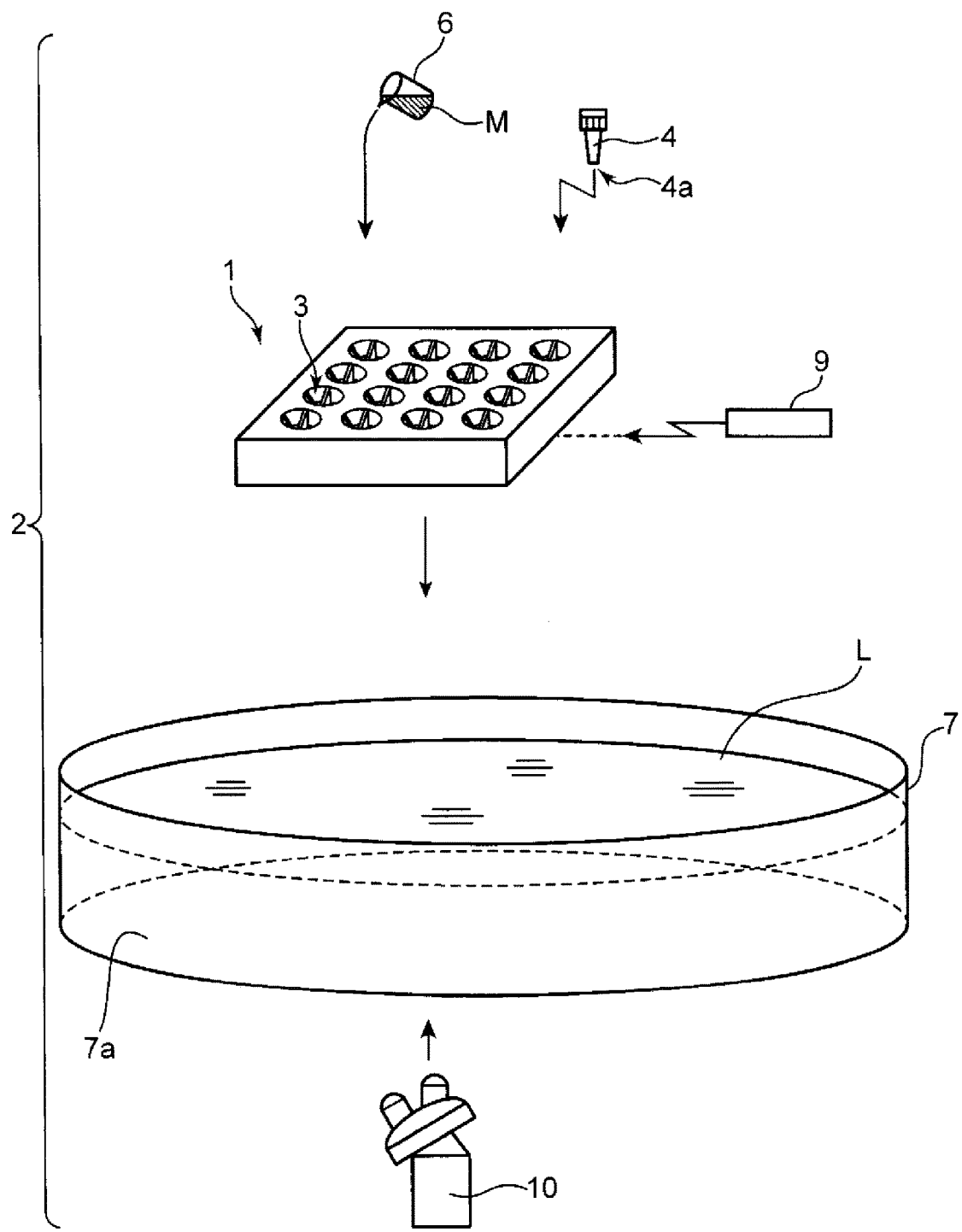
FIG. 3 is a view showing a suction device provided with the well plate according to the first embodiment of the present disclosure.
Figure 4A:
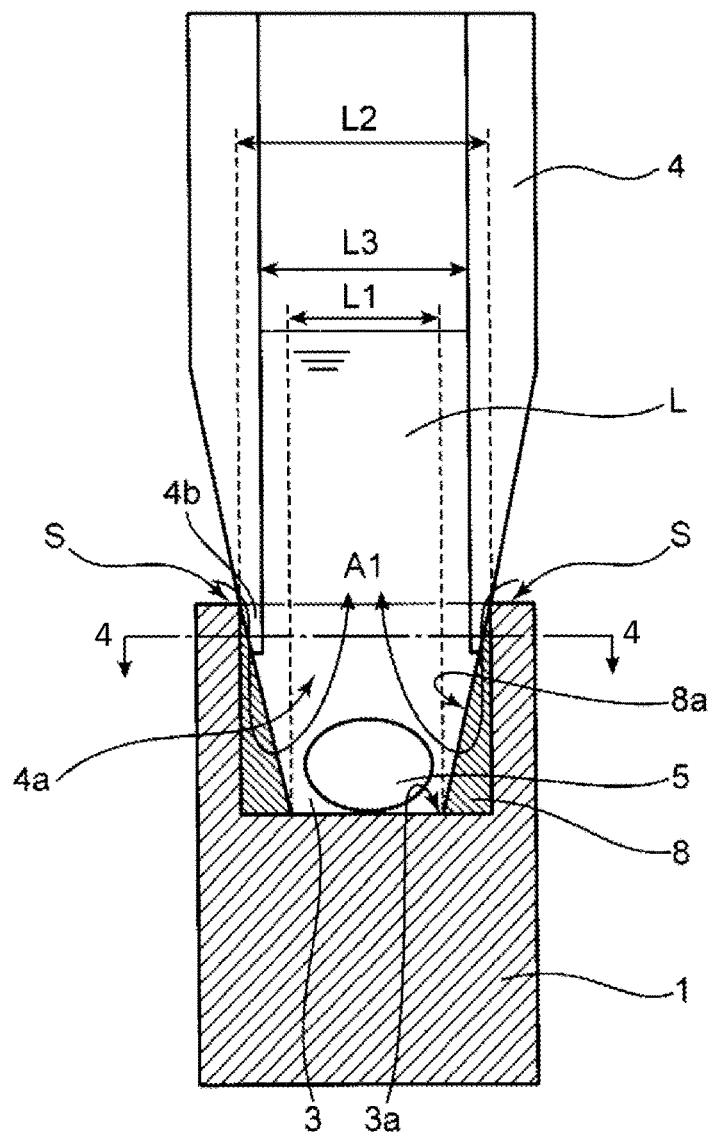
FIGS. 4A and 4B are views showing a state of sucking a subject held in the well plate according to the first embodiment of the present disclosure.
Figure 4B:
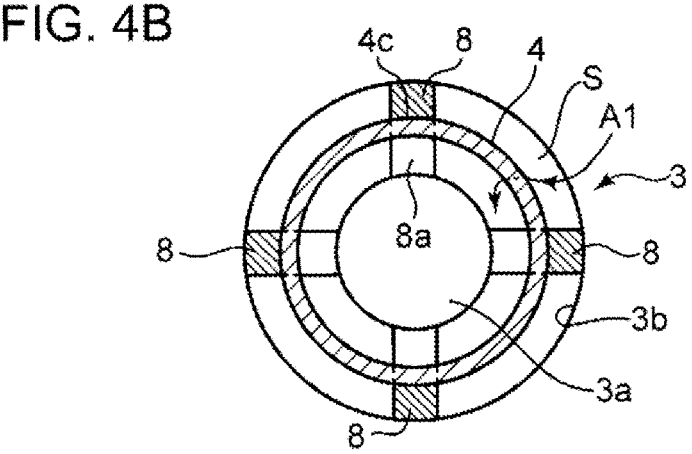

Hereinafter, a well plate 1 and a suction device 2 provided with the well plate 1 according to a first embodiment of the present disclosure are described in detail with reference to the drawings. FIG. 1 is a perspective view of the well plate 1 according to the first embodiment of the present disclosure. FIGS. 2A and 2B are views showing wells 3 of the well plate 1 of this embodiment, wherein FIG. 2A is a sectional view of the well plate 1 of this embodiment along 2-2 in FIG. 1 and FIG. 2B is a plan view of the well 3 formed in the well plate 1 of this embodiment. FIG. 3 is a view showing the suction device 2 provided with the well plate 1 according to this embodiment. FIG. 4A is a view showing a state of sucking a subject 5 held in the well plate 1 of this embodiment. FIG. 4B is a sectional view along 4-4 of FIG. 4A.

As shown in FIGS. 1 to 3, the well plate 1 of this embodiment is used by being immersed in liquid L and includes the wells 3. The well 3 holds the subject 5 to be sucked by a suction nozzle 4 including a suction port 4a on an inner bottom part 3a. The well 3 is provided with ribs 8 (clearance forming member) for forming clearances S through which the liquid L flows in a state where a tip part 4b of the suction nozzle 4 including the suction port 4a is inserted into and held in contact with the well 3 (see FIG. 4A). The configurations of the well plate 1 and the suction device 2 provided with the well plate 1 according to this embodiment are described below.

Collection of Subjects M

A collection of subjects M is liquid containing subjects 5. The collection of subjects M is normally stored in a storage container 6 such as a beaker (see FIG. 3). The collection of subjects M stored in the storage container 6 is added from above the well plate 1 immersed in a container 7 storing the liquid L.

A method for adding the collection of subjects M is not particularly limited. For example, in terms of eliminating the drying of the subjects and physical impacts, a user preferably gently adds the collection of subjects M from a position close to the liquid surface of the liquid L stored in the container 7 or directly adds them to the liquid L using a suction/discharge device such as a suction pipette. The collection of subjects M added to the liquid L gently precipitates by gravity while being dispersed in the liquid L. Thus, physical impacts on the subjects 5 are reduced.

The type of the subjects 5 is not particularly limited, and examples thereof include mixtures of particles having various shapes and particle diameters, cell culture solutions and cell treatment solutions containing cells and impurities having various sizes. For example, if the collection of subjects M is mixed slurry of particles having various shapes, the subjects 5 are particles contained in the mixed slurry. If particles of a shape desired by the user are included in these particles, such desired particles fall under the subjects 5. Similarly, if the collection of subjects M is a cell culture solution or the like containing cells and impurities having various sizes and only the cells are sucked, the subjects 5 are the cells contained in this cell culture solution or the like. Further, if cells of a shape desired by the user are included in these cells, such desired cells fall under the subjects 5.

The subjects 5 to be held using the well plate 1 of this embodiment are preferably bio-based cells, more preferably bio-based cell aggregates.

The well plate 1 of this embodiment can hold bio-based cells, which are subjects having large shape deviations, in the wells 3. The subjects 5 held in the wells 3 can be easily sucked and collected by the user using a suction/discharge device such as a suction pipette. The well plate 1 of this embodiment can suck the liquid L around through the clearances S formed by providing the ribs 8 to be described later in collecting the subject 5 held in the well 3. Thus, the subject 5 held in the well 3 is efficiently sucked through the suction port 4a along the flow of the sucked liquid L. As a result, the well plate 1 of this embodiment can contribute to operation efficiency in the fields of bio-related technology and medicine.

If the subject 5 is a bio-based cell aggregate (spheroid), a biosimilar environment considering interactions among cells is reconfigured in the cell aggregate. A test result obtained using a cell aggregate considers functions of individual cells as compared with a test result obtained using one cell. Further, in the case of using a cell aggregate, the user can make experiment conditions uniform in accordance with an environment in a biological body. Thus, if cell aggregates are held and collected using the well plate 1 of this embodiment, the user can prepare specimens capable of providing a highly reliable result in the fields of bio-related technology and medicine.

The size of the subject 5 is not particularly limited. The subject 5 may be so sized as to entirely precipitate to the inner bottom part 3a of the well 3 (see FIG. 4A) or may be so sized as to be partly held in contact with the well 3. Although described in detail later, a diameter (L2) of an opening of the well 3 is 700 to 2500 μm and a distance (L1) between a pair of ribs 8 facing each other on the inner bottom part 3a of the well 3 is 80 to 800 μm as shown in FIG. 2B. Thus, a diameter of the subject 5 is about 80 to 800 μm.

Container 7

The container 7 stores the liquid L. In FIG. 3 is illustrated the container 7 formed of a bottomed cylindrical body including an inner bottom part 7a and an open upper end.

The shape of the container 7 is not particularly limited, but a flat shape including the inner bottom part 7a in the form of a flat surface and having a height relatively shorter than a lateral width is preferably adopted in view of operability and safety.

An opening width and a height (depth) of the container 7 may be such that the liquid L can be stored to such an extent that the above well plate 1 can be completely immersed.

The material of the container 7 is not particularly limited, but a translucent material is preferably used in terms of a possibility to easily confirm a state of the subjects 5 held in the wells 3 of the well plate 1 housed in the container 7. The translucent material is described in detail in the later description of the well plate 1. Further, if both the container 7 and the well plate 1 are made of a translucent material, operation efficiency can be improved since the user can continuously observe the subjects 5 using a phase-contrast microscope 10 from below the container 7 and make a judgment.

A circular glass dish having a height of several mm to several cm and a diameter of about 10 cm can be used as the container 7 satisfying these conditions.

The liquid L to be stored in the container 7 is not particularly limited as long as it does not deteriorate properties of the subjects 5 and can be appropriately selected according to the type of the subjects 5. Typical examples of the liquid L may include, for example, cell freezing solutions such as glycerol to be added before refrigeration storage and Cell Bankers (produced by Juji Field Inc.), formalin, reagents for fluorescent staining, antibodies, purified water and physiological saline solution in addition to media such as basic media, synthetic media, Eagle's media, RPMI media, Fischer's media, Ham's media, MCDB media and serums.

If the subjects 5 are cells, a culture preservation solution matching properties of the cells can be used. For example, in the case of using BxPC-3 (human pancreatic tumor cells), which are bio-based cells, as the subjects 5, a mixture of a RPMI-1640 medium with 10% of FBS (Fetal Bovine Serum), to which a supplement such as antibiotic or sodium pyruvate is added if necessary, can be used as the liquid L.

A quantity of the liquid L to be stored in the container 7 is not particularly limited and it is sufficient to store such a quantity of the liquid L that the well plate 1 to be described later can be completely immersed and a liquid flow can be generated around the subject 5 when the user sucks the subject 5 held in the well 3 by operating the suction nozzle 4.

Note that, in using the well plate 1 of this embodiment, the user can store the liquid L having the same components as the liquid included in the collection of subjects M in the container 7.

Further, the user may place the well plate 1 of this embodiment on the inner bottom part 7a of the container 7 storing no liquid L and add the collection of subjects M from above the well plate 1. In this case, some of the subjects 5 precipitate into the wells 3 simultaneously with the addition. Further, the remaining subjects 5 not held in the wells 3 drip down to the inner bottom part 7a of the container 7 from the well plate 1 together with the liquid included in the collection of subjects M. The user may suck the subjects 5 from the collection of subjects M dripped down to the inner bottom part 7a of the container 7 using a suction/discharge device such as a suction pipette attached with the suction nozzle 4 and add them again from above the well plate 1 when judging that an insufficient number of the subjects 5 are held in the wells 3 and there are empty wells 3. As described later, in the case of holding the subjects 5 in the wells 3 using the well plate 1 of this embodiment, the user collects the subject 5 while sucking the liquid L around the well 3 through the clearances S in collecting the subject 5 held in the well 3. Thus, the liquid included in the collection of subjects M is preferably in a quantity sufficient to immerse the well plate 1 placed in the container 7.

Well Plate 1

As shown in FIGS. 1 and 3, the well plate 1 is used by being immersed in the liquid L stored in the container 7 and includes the wells 3. The wells 3 are provided to make the subjects having a specific shape selectable out of the subjects 5 included in the collection of subjects M. The well plate 1 illustrated in FIG. 1 has a flat rectangular parallelepipedic shape with an upper surface 1a and a bottom surface 1b, and the wells 3 each including the inner bottom part 3a and recessed toward the bottom surface 1b from the upper surface 1a are arranged in a 4×4 matrix. The user causes the subjects 5 to be held in the wells 3 and determines the presence or absence of the subject 5 held in the well 3 and the shape of the subject 5 from above or below the well 3 using the phase-contrast microscope 10 (determining device) to be described later.

The shape of the well plate 1 is not particularly limited, but is preferably a flat shape since the well plate 1 is easily immersed in the container 7 and easily holds the subjects 5 precipitating directly below by gravity if the container 7 has a flat shape and since the subjects 5 are easily focused within a depth of field of an objective lens of the phase-contrast microscope 10 when the subjects 5 held in the wells 3 of the well plate 1 are observed.

A width of the well plate 1 has only to be smaller than the opening width of the container 7 and a height thereof has only to be smaller than a depth of the container 7 since the well plate 1 needs to be immersed in the liquid L stored in the container 7.

The material of the well plate 1 is not particularly limited, but a translucent material is preferably used since a state of its contents can be easily confirmed. Further, if both the container 7 and the well plate 1 are made of a translucent material, the subjects 5 can be continuously observed from above or below the container 7 by a phase-contrast microscope 10.

The translucent material is not particularly limited, but it is preferable to use, for example, thermoplastic resins, thermosetting resins and photocurable resins. More specifically, the examples of the translucent material include polyethylene resins; polyethylene naphthalate resins; polypropylene resins; polyimide resins; polyvinyl chloride resins; cycloolefin copolymers; norbornene-containing resins; polyether sulfone resins; polyethylene naphthalate resins; cellophanes; aromatic polyamide resins; (meth)acrylic resins such as polymethyl (meth)acrylates; styrene resins such as polystyrenes and styrene-acrylonitrile copolymers; polycarbonate resins; polyester resins; phenoxy resins; butyral resins; polyvinyl alcohols; cellulose-based resins such as ethyl cellulose, cellulose acetate and cellulose acetate butyrate; epoxy resins; phenol resins; silicone resins; and polylactic acids.

It is also preferable to use inorganic materials such as metal alkoxides, ceramic precursor polymers, solutions obtained through hydrolysis polymerization of solutions containing metal alkoxides by a sol-gel method, or inorganic materials obtained by solidifying combinations of these such as inorganic materials having a siloxane bond (polydimethylsiloxane, etc.) and glass.

Soda glass, quartz, borosilicate glass, Pyrex (registered trademark) glass, low melting point glass, photosensitive glass and other optical glasses having various refractive indices and Abbe numbers can be widely used as the glass.

Well 3

The well 3 is a recess having a substantially cylindrical shape and formed in the upper surface 1a of the well plate 1. The well 3 includes the inner bottom part 3a on the bottom surface. In this embodiment are illustrated the wells 3 arranged in a 4×4 matrix.

The number of the wells 3 is not particularly limited. One well may be formed or a plurality of wells 3 may be arranged in the well plate 1. In the case of arranging a plurality of wells 3, it is preferable to arrange them in a matrix. By arranging the plurality of wells 3 in this way, the user can cause a plurality of subjects 5 to be simultaneously arranged and held in the wells 3 and improve operation efficiency.

The size (diameter of the opening) of the well 3 is not particularly limited. As shown in FIGS. 2A and 2B, the diameter (L2) of the opening of the well 3 is 700 to 2500 μm, and the distance (L1) between the pair of ribs 8 to be described later and facing each other on the inner bottom part 3a of the well 3 is 80 to 800 μm.

A depth of the well 3 is not particularly limited and may be such that the subject 5 can be held in the well 3 as shown in FIG. 2A. As described above, since the diameter of the subject 5 is about 80 to 800 μm, the depth of the well 3 is, for example, about 160 to 1600 μm.

As shown in FIGS. 4A and 4B, the well 3 includes the ribs 8 for forming the clearances S through which the liquid L flows in the state where the tip part 4b of the suction nozzle 4 including the suction port 4a is inserted into and held in contact with the well 3.

As show in FIG. 4B, the clearance S is a space formed between an outer wall 4c of the suction nozzle 4 and an inner wall 3b of the well 3 when the tip part 4b of the suction nozzle 4 including the suction port 4a is inserted into the well 3. Specifically, if the tip part 4b of the suction nozzle 4 is inserted into the well 3 formed with no rib 8, the outer wall 4c of the suction nozzle 4 and the inner wall 3b of the well 3 are held in close contact without forming any clearance. However, since the well 3 formed in the well plate 1 of this embodiment includes the ribs 8 on parts of the inner wall 3b, sloped parts 8a of the ribs 8 and the outer wall 4c of the suction nozzle 4 come into contact, but the outer wall 4c of the suction nozzle 4 and the inner wall 3b of the well 3 face each other while being separated. As a result, spaces formed between the outer wall 4c of the suction nozzle 4 and the inner wall 3b of the well 3 serve as the clearances S. The liquid L can flow through the formed clearances S even when the user inserts the suction nozzle 4 into the well 3 and brings parts of the outer wall 4c of the suction nozzle 4 into contact with the ribs 8. An arrow A1 shows a flow of the liquid L flowing into the well 3 through the clearance S and sucked through the suction port 4a with the suction nozzle 4 inserted in the well 3.

By including the ribs 8, the well plate 1 of this embodiment enables the subject 5 to come into contact with the ribs 8 formed in the well 3 and be stably held and enables the tip part 4b of the suction nozzle 4 to be stably held in position (suction position) by bringing the ribs 8 into contact with the parts of the outer wall 4c of the suction nozzle 4.

Further, as described above, the well plate 1 of this embodiment can form the clearances S, through which the liquid L can flow, near a contact position even in the state where the tip part 4b of the suction nozzle 4 including the suction port 4a is inserted into and held in contact with the well 3. The suction nozzle 4 can suck the liquid L around through the clearances S formed by the ribs 8. As a result, the subject 5 held in the well 3 is efficiently sucked through the suction port 4a of the suction nozzle 4 along the flow of the sucked liquid. Since a groove or the like is not formed on the cylindrical inner wall 3b or the inner bottom part 3a in the well 3, the subject 5 is neither fitted into nor caught by a part of the well 3 even if it has a soft property.

As shown in FIGS. 2A and 2B, the rib 8 is formed to extend upward toward the opening from the inner bottom part 3a of the well 3 and includes the sloped part 8a on its part. A projecting length (L4) of the sloped part 8a from the inner wall 3b of the well 3 is longer near the inner bottom part 3a than near the opening.

As shown in FIG. 2B, the ribs 8 are so formed at four positions on the inner wall 3b of the well 3 that circumference distances between adjacent ribs 8 are substantially equal. The sloped parts 8a are downward inclined surfaces to reduce an opening area of the well 3 from the opening of the well 3 toward the inner bottom part 3a. Thus, the ribs 8 each including the sloped part 8a make the subject 5 be easily introduced into the well 3 and easily generate the flow of the liquid L around the subject 5 when the user sucks the subject 5 using the suction nozzle 4.

As described above, the projecting length (L4) of the sloped part 8a from the inner wall 3b of the well 3 is longer at the inner bottom part 3a than at the opening of the well 3. Thus, as shown in FIG. 2B, the distance (L1) between the pair of ribs 8 facing each other on the inner bottom part 3a of the well 3 is shorter than a diameter (L3) of a cross-section of the suction port 4a formed in the tip part 4b of the suction nozzle 4 to be described later. Denoted by P is the position of the tip part 4b when the tip part 4b of the suction nozzle 4 including the suction port 4a is inserted into the well 3. As a result, when the user inserts the tip part 4b of the suction nozzle 4 into the well 3, the tip part 4b of the suction nozzle 4 does not reach the inner bottom part 3a of the well 3 and is stopped in contact with the sloped parts 8a of the ribs 8. Thus, the tip part 4b of the suction nozzle 4 does not come into contact with the subject 5 held on the inner bottom part 3a of the well 3 and the subject 5 is not damaged by the tip part 4b of the suction nozzle 4.

A maximum value of the projecting length (L4) of the sloped part 8a projecting from the inner wall 3b of the well 3 is, for example, about 300 to 1300 μm although it varies according to the size of the well 3 (diameter of the opening) and the diameter of the subject 5 to be held.

The number of the ribs 8 is not particularly limited and one rib 8 may be formed on the inner wall 3b of the well 3 or a plurality of ribs 8 may be formed on the inner wall 3b of the well 3 in the well plate 1 of this embodiment. When a plurality of ribs 8 are formed, the user can more stably position the suction nozzle 4 than when one rib 8 is formed. Further, since the plurality of ribs 8 can form more clearances S, the flow of the liquid L is easily generated in sucking the subject 5 by the suction nozzle 4.

In the case of forming the plurality of ribs 8, the arrangement of the ribs 8 is not particularly limited. In the well plate 1 of this embodiment, the user can form the ribs 8 such that the circumference distances between adjacent ribs 8 are substantially equal or different in the case of arranging the plurality of ribs 8 on the inner wall 3b of the well 3.

In the case of forming the plurality of ribs 8 at equal intervals on the inner wall 3b of the well 3, the sizes (widths) of the clearances S formed by the respective ribs 8 and the suction nozzle 4 are uniform. Thus, the user can make liquid flows generated in the clearances S at the time of suction uniform. On the other hand, in the case of forming the ribs 8 such that the circumferential distances between adjacent ribs 8 are different, the sizes (widths) of the clearances S formed by the respective ribs 8 and the suction nozzle 4 are nonuniform. Thus, the user can change liquid flows generated in the clearances S at the time of suction in a nonuniform manner. As a result, if the well plates 1 including the wells 3 formed with the ribs 8 in different arrangements are prepared, the user can select the well plate 1 capable of generating liquid flows, which make the suction of the subjects 5 easier, in accordance with the shapes of the subjects 5 desired to be held.

Suction Device 2

The suction device 2 includes the aforementioned container 7, the aforementioned well plate 1 to be immersed in the container 7, and the suction nozzle 4 including the suction port 4a for sucking the subject 5 held in the well 3 formed in the well plate 1. As described above, the well 3 is provided with the ribs 8 for forming the clearances S for allowing the liquid L to flow in the state where the tip part 4b of the suction nozzle 4 including the suction port 4a is inserted into and held in contact with the well 3. Further, the suction device 2 of this embodiment includes a vibration generating mechanism (vibration generating device). The suction device 2 further includes the phase-contrast microscope 10 for observing the subjects 5 held in the well plate 1 from above or below the container 7. Each component is described below. Note that the container 7 and the well plate 1 are not described since they are the same as those described above.

Suction Nozzle 4

The suction nozzle 4 is a nozzle for sucking and collecting the subject 5 held in the well 3 with the suction port 4a formed in the tip part 4b. The suction nozzle 4 is connected to a pump mechanism (not shown) provided outside. The pump mechanism generates a suction force at the suction port 4a formed in the tip part 4b of the suction nozzle 4. The subject 5 sucked to the suction port 4a is held in the suction port. Note that the liquid L sucked before the subject 5 is sucked passes through a tubular passage (not shown), which is a suction passage provided in the suction nozzle 4, and is held near a nozzle tip in the tubular passage, or stored in a storage portion (not shown) provided on a downstream side of the tubular passage, or discarded, or discharged to the container 7 again by a separately provided circulation passage (not shown).

As shown in FIG. 3, the suction nozzle 4 is so disposed that the tip part 4b including the suction port 4a is insertable into the opening of the well 3 from above the well plate 1. One suction nozzle 4 is illustrated in FIG. 3.

The number of the suction nozzles 4 is not particularly limited and may be one or more. If there are a plurality of wells 3 formed in the well plate 1, the suction nozzles 4 are preferably arranged at an interval corresponding to the arrangement of the respective wells 3. Further, if the wells 3 are arranged in a matrix as shown in FIG. 1, the suction device 2 of this embodiment preferably includes four suction nozzles 4 prepared and arranged in a row for a design capable of sucking the subjects 5 at once in each row of the wells 3 or suction nozzles 4 prepared and arranged in a 4×4 matrix for a design capable of sucking the subjects 5 in all the wells 3 at once. By adopting a configuration capable of collecting a plurality of subjects 5 at once in this way, the user can improve operation efficiency.

A cross-sectional shape of the suction port 4a formed in the tip part 4b of the suction nozzle 4 of the suction device 2 of this embodiment is a circular shape as shown in FIG. 2B. The cross-sectional shape of the suction port 4a is not particularly limited and may be an elliptical shape or a rectangular shape.

As described above, the diameter (L3) of the cross-section of the suction port 4a formed in the tip part 4b of the suction nozzle 4 is longer than the distance (L1) between the pair of ribs 8 on the inner bottom part 3a of the well 3 and shorter than the diameter (L2) of the opening of the well 3. Thus, parts of the outer wall 4c of the tip part 4b of the suction nozzle 4 come into contact with the sloped parts 8a of the ribs 8 as shown in FIGS. 4A and 4B when the tip part 4b of the suction nozzle 4 including the suction port 4a is inserted into the well 3, but other parts of the outer wall 4c are separated from the inner wall 3b of the well 3. As a result, the clearances S are formed between the parts of the outer wall 4c of the suction nozzle 4 and the inner wall 3b of the well 3.

The clearances S cause the liquid L present around the well 3 to flow into the well 3 when the user generates a suction force in the suction port 4a by operating the suction nozzle 4. The liquid L flowing into the well 3 through the clearances S generates a liquid flow around the suction port 4a by the suction force generated in the suction port 4a. The subject 5 held in the well 3 is sucked through the suction port 4a together with the generated liquid flow.

The size of the clearances S is not particularly limited, but a total of the areas of the formed clearances S is, for example, about 0.3 to 9 mm². If the clearances S of such a size are formed, the suction device 2 of this embodiment can generate such a water flow as to suck the subject 5 at the time of suction using a suction/discharge device such as a suction pipette provided with a normal suction tip as the suction nozzle 4.

Vibration Generating Mechanism 9

The vibration generating mechanism 9 vibrates the well plate 1 in the state where the tip part 4b of the suction nozzle 4 including the suction port 4a is inserted into and held in contact with the well 3. Specifically, the vibration generating mechanism 9 causes the subject 5 held in the well 3 to temporarily float, so that the subject 5 is easily moved with the flow of the liquid L flowed into the well 3 through the clearances S when being sucked through the suction nozzle 4. Further, the vibration generating mechanism 9 applies vibration to the subject 5 precipitating in the well 3 or precipitated near the opening of the well 3 by generating vibration, thereby urging the subject 5 to precipitate to the inner bottom part 3a of the well 3.

As shown in FIG. 3, the vibration generating mechanism 9 is connected to the well plate 1. Note that the disposed position of the vibration generating mechanism 9 is not particularly limited. If the well plate 1 is fixed to the inner bottom part 7a of the container 7 and there is no likelihood of stirring up impurities other than the subjects 5 even if the container 7 is vibrated, the vibration generating mechanism 9 may be connected to the container 7 and indirectly vibrate the well plate 1 by vibrating the container 7. Further, the vibration generating mechanism 9 may be provided for each of the well plate 1 and the container 7.

The suction device 2 of this embodiment can cause the subjects 5 to temporarily float by applying vibration to the subjects 5 held in the wells 3. As a result, the floating subject 5 is easily sucked by the suction nozzle 4, wherefore efficiency in sucking and collecting the subjects 5 by the user is improved.

In addition to a method for generating physical vibration by a vibrator, a method for vibrating the subjects 5 by applying electromagnetic waves and a method for vibrating the subjects 5 by applying ultrasonic waves without affecting the properties of the subjects 5 can be adopted as a vibration generating method by the vibration generating mechanism 9.

Phase-Contrast Microscope 10

The phase-contrast microscope 10 is provided to observe and determine whether or not the subjects 5 are held in the well plate 1 and the shapes of the held subjects 5 from above or below the container 7. As just described, by observing and determining the subjects 5 using the phase-contrast microscope 10, the user can easily confirm the presence of the subjects 5 held in the wells 3. Further, the user can confirm the shapes of the subjects 5 held in the wells 3 before suction. Thus, if the subject 5, which is not supposed to be sucked due to a distorted shape or the like, is held in the well 3, the user can eliminate it from suction targets. Furthermore, the user can easily confirm the positions of the suction port 4a of the suction nozzle 4 and the openings of the wells 3 and perform accurate suction.

Note that although the phase-contrast microscope 10 is adopted as a determining device in this embodiment, the determining device is not particularly limited. Besides general optical microscopes, fluorescence microscopes, polarization microscopes, stereomicroscopes, bright-field microscopes, dark-field microscopes, differential interference microscopes, supersonic microscopes, confocal microscopes, laser scanning microscopes, electronic microscopes, scanning probe microscopes, X-ray microscopes, virtual microscopes, digital microscopes and the like can be used.

In the case of observing the subjects 5 with high transparency such as cells, the phase-contrast microscope 10 or a fluorescence microscope is preferably used as the determining means. In the case of using a fluorescence microscope as the determining device, the subjects 5 need to be fluorescent. Thus, in the case of measuring the non-fluorescent subjects 5 by the fluorescence microscope, the subjects 5 are measured after being dyed with a fluorescent dye. A method for dyeing the subjects 5 is not particularly limited and a preferable dyeing method may be appropriately adopted. For example, chemical fluorescent staining, antibody fluorescent staining or a like method can be adopted. Besides, it is also possible to adopt a method for introducing a gene inducing fluorescent protein such as green fluorescent protein (GFP) into a cell through genetic recombination and observing the cell.

A motor device (not shown) is attached to the phase-contrast microscope 10. The motor device includes an imaging element for converting an optical image generated by the phase-contrast microscope 10 into an electrical image data signal, an image processor for applying image processings such as a gamma correction and a shading correction to the image data, and a display device for displaying the image data after the image processings.

Determination criteria in determining the shapes of the subjects 5 by the phase-contrast microscope 10 are not particularly limited. The determination criteria may be appropriately determined by the user depending on the use application of the subjects 5.

Note that although the liquid L is stored in the wells 3 by immersing the well plate 1 in the container 7 in this embodiment, a method for storing the liquid L in the wells 3 is not particularly limited. For example, the liquid L may be stored only in the wells 3 without immersing the well plate 1 in the liquid L. In this case, there is a possibility that the subject 5 cannot be sufficiently sucked due to an insufficient quantity of the liquid L when the user sucks the subject 5 held in the well 3 if the liquid L is stored only in the well 3. In such a case, the well plate 1 of this embodiment may be provided with an outer wall (not shown) to cover the upper surface of the well plate 1 and the openings of the respective wells 3 and the inside of this outer wall may be filled with the liquid L. This enables the user to collect the subjects 5 held in the wells 3 together with a sufficient quantity of the liquid L.

Second Embodiment

Figure 5A:
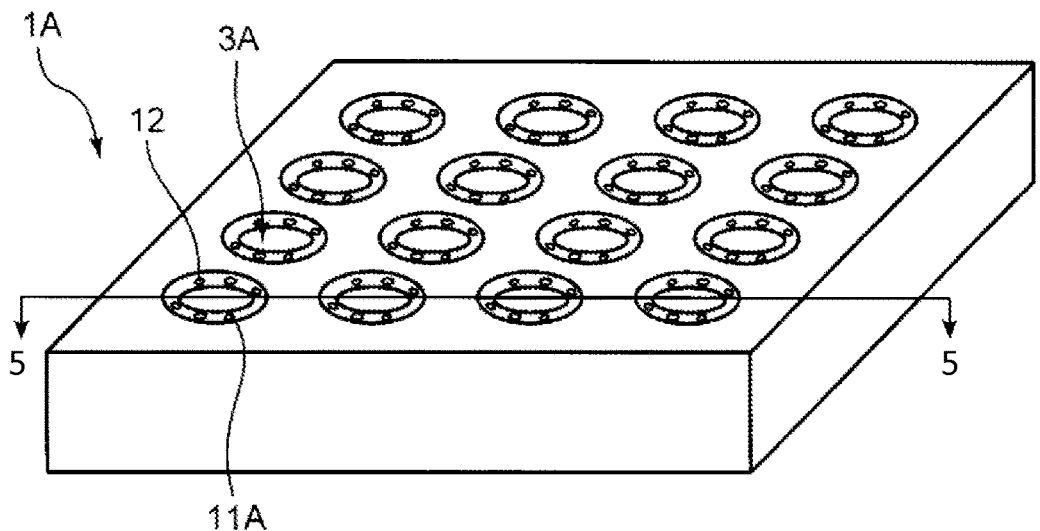
FIGS. 5A, 5B and 5C are views of a well plate according to a second embodiment of the present disclosure.
Figure 5B:
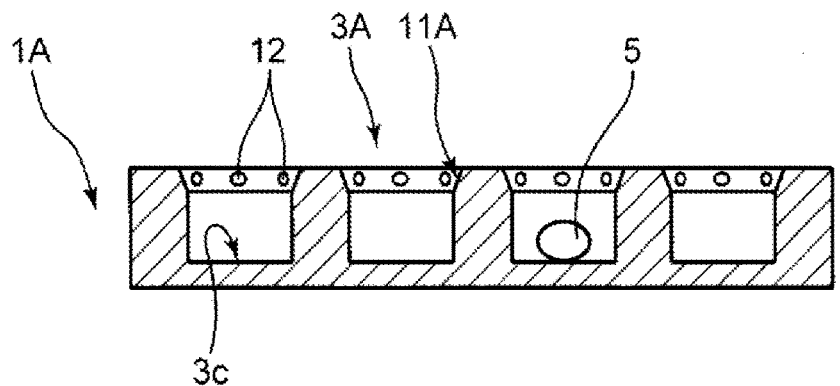
Figure 5C:
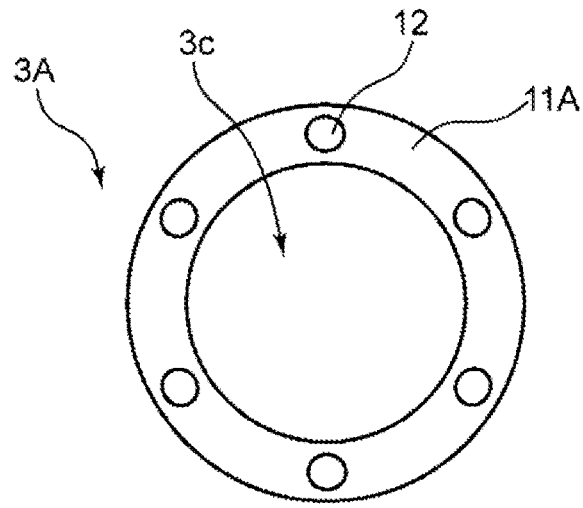

A well plate 1A of a second embodiment of the present disclosure is described in detail with reference to the drawings. FIGS. 5A, 5B and 5C are views of the well plate 1A of this embodiment. FIG. 5A is a perspective view of the well plate 1A of this embodiment, FIG. 5B is a sectional view along 5-5 of FIG. 5A and FIG. 5C is a plan view of a well 3A of this embodiment.

The well plate 1A of this embodiment is configured similarly to the well plate 1 of the first embodiment except that the configuration of the wells 3A is different. Thus, only points of difference are described.

As shown in FIGS. 5A and 5B, the well 3A formed in the well plate 1A of this embodiment has a substantially cylindrical shape and includes a tapered part 11A for reducing an opening area of the well 3A from an opening of the well 3A toward an inner bottom part 3c. The tapered part 11A is formed with a plurality of projections 12.

Since the tapered part 11A is a downward inclined surface from the opening of the well 3A toward an inner bottom part 3a as shown in FIG. 5B, a subject 5 is easily introduced into the well 3A. Specifically, when a user adds the subject 5 from above the well plate 1A, the subject 5 precipitated near the opening of the well 3A is introduced into the well 3A by being guided down along the tapered part 11A.

Further, if the opening of the well 3A is an upper end part of the tapered part 11A, the tapered part 11A comes into contact with an outer wall 4c of a tip part 4b of a suction nozzle 4 including a suction port 4a at a lower end part of the tapered part 11A. Thus, the user can confirm a contact state of the outer wall 4c of the tip part 4b of the suction nozzle 4 and the tapered part 11A and position the suction nozzle 4 when inserting the suction nozzle 4 into the well 3A.

Note that although the outer wall 4c of the tip part 4b of the suction nozzle 4 comes into contact with the lower end part of the tapered part 11A in this embodiment, the contact position of the tapered part 11A and the outer wall 4c is not limited to the lower end part of the tapered part 11A. For example, depending on the shape of the outer wall 4c of the tip part 4b of the suction nozzle 4, the outer wall 4c may come into contact with an inclined part of the tapered part 11A other than the lower end part. Even in such a case, the user can confirm the contact state of the outer wall 4c of the tip part 4b of the suction nozzle 4 and the tapered part 11A and position the suction nozzle 4 when inserting the suction nozzle 4 into the well 3A.

The projections 12 are provided on the tapered part 11A. As shown in FIG. 5C, six projections 12 are so provided that circumferential separation distances between the projections 12 adjacent at substantially center positions between the upper end part and the lower end part of the tapered part 11A are substantially equal.

The number of the projections 12 is not particularly limited and the well plate 1A of this embodiment may be formed with one projection 12 on the tapered part 11A or a plurality of projections 12 on the tapered part 11A in the well plate 1 of this embodiment. When a plurality of projections 12 are formed, the user can more stably position the suction nozzle 4 than when one projection 12 is formed. Further, since the plurality of projections 12 can form more clearances S, a flow of liquid L is easily formed in sucking the subject 5 by the suction nozzle 4.

In the case of forming the plurality of projections 12, the arrangement of the projections 12 is not particularly limited. The well plate 1A of this embodiment can be so formed that the circumference distances between adjacent projections 12 are substantially equal or different in the case of forming the plurality of projections 12 on the tapered part 11A.

In the case of forming the plurality of projections 12 at equal intervals on the tapered part 11A, the sizes (widths) of the clearances S formed by the respective projections 12 and the suction nozzle 4 are uniform. Thus, the user can make liquid flows generated in the clearances S at the time of suction uniform. On the other hand, in the case of forming the projections 12 such that the circumferential distances between adjacent projections 12 are different, the sizes (widths) of the clearances S formed by the respective projections 12 and the suction nozzle 4 are nonuniform. Thus, the user can change the liquid flows generated in the clearances S at the time of suction in a nonuniform manner. As a result, if the well plates 1A including the wells 3A formed with the projections 12 in different arrangements are prepared, the user can select the well plate 1A capable of generating liquid flows, which make the suction of the subjects 5 easier, in accordance with the shapes of the subjects 5 desired to be held.

A height (length of a perpendicular drawn from an apex of the projection 12 to the tapered part 11A) of the projection 12 is not particularly limited and may be any height as long as the opening of the well 3 is not covered by the projections 12. For example, if a diameter of the opening of the well 3A at the lower end part of the tapered part 11A is 80 to 800 μm, the height of the projection 12 is about 200 to 600 μm.

The shape of the projection 12 is not particularly limited and may be a regular shape such as a semispherical shape, a semiellipsoidal shape, a conical shaped or a rectangular parallelepipedic shape or may be an irregular shape.

A method for forming the projections 12 on the tapered part 11A is not particularly limited and the projections 12 may be integrally formed to the tapered part 11A or may be bonded to the tapered part 11A after being formed as separate bodies.

Third Embodiment

Figure 6A:
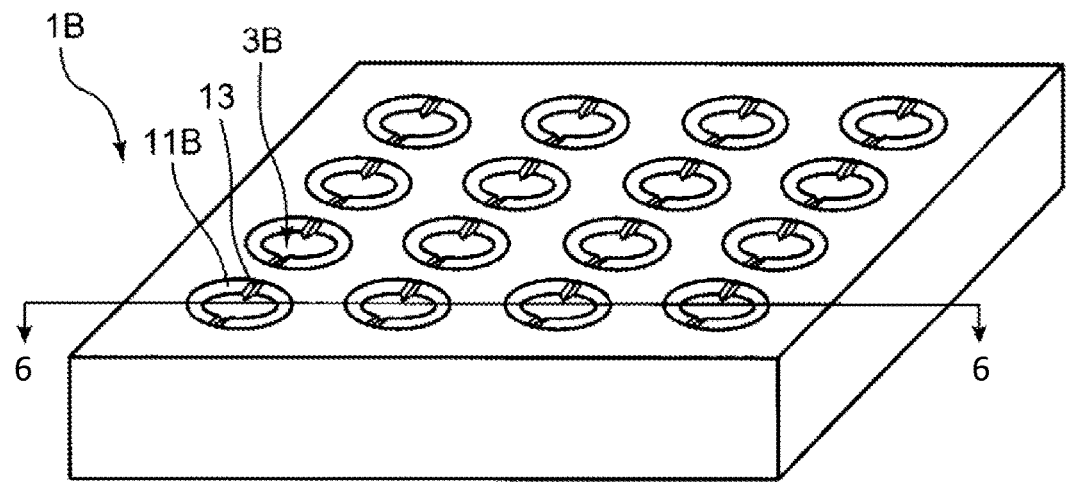
FIGS. 6A, 6B, 6C and 6D are views of a well plate according to a third embodiment of the present disclosure.
Figure 6B:
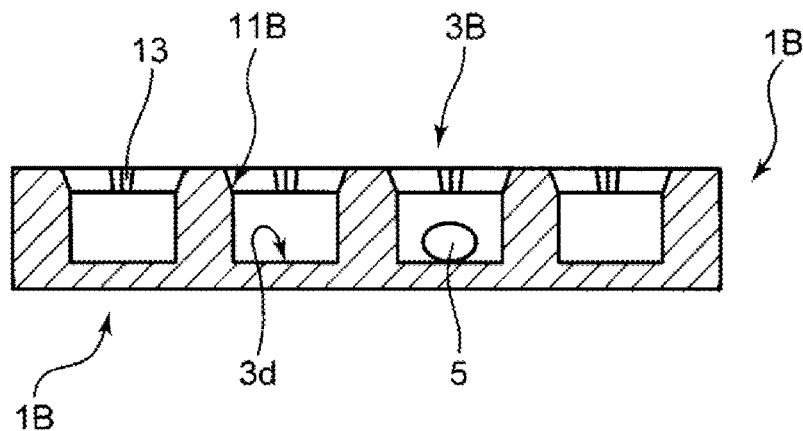
Figure 6C:
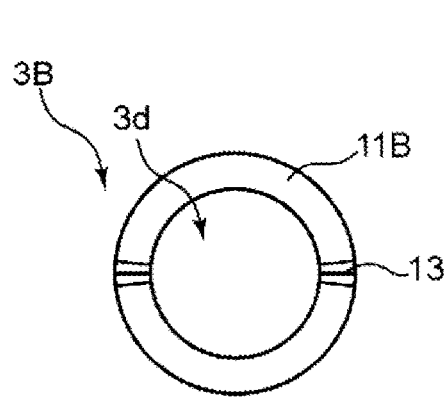

A well plate 1B of a third embodiment of the present disclosure is described in detail with reference to the drawings. FIGS. 6A-6D are views of the well plate 1B of this embodiment. FIG. 6A is a perspective view of the well plate 1B of this embodiment, FIG. 6B is a sectional view along 6-6 of FIG. 6A and FIG. 6C is a plan view of a well 3B of this embodiment.

The well plate 1B of this embodiment is configured similarly to the well plate 1 of the first embodiment except that the configuration of the wells 3B is different. Thus, only points of difference are described.

As shown in FIGS. 6A and 6B, the well 3B formed in the well plate 1B of this embodiment has a substantially cylindrical shape and includes a tapered part 11B for reducing an opening area of the well 3B from an opening of the well 3B toward an inner bottom part $3d$. The tapered part 11B is formed with a plurality of grooves 13.

Since the tapered part 11B is a downward inclined surface from the opening of the well 3B toward the inner bottom part $3d$ as shown in FIG. 6B, a subject 5 is easily introduced into the well 3B. Specifically, when a user adds the subject 5 from above the well plate 1B, the subject 5 precipitated near the opening of the well 3B is introduced into the well 3B by being guided down along the tapered part 11B.

Further, if the opening of the well 3B is an upper end part of the tapered part 11B, the tapered part 11B comes into contact with a tip part $4b$ of the suction nozzle 4 at a lower end part of the tapered part 11B. Thus, the user can position the suction nozzle 4 when inserting the suction nozzle 4 into the well 3B.

Note that inclined parts other than the lower end part of the tapered part 11B can also come into contact with an outer wall $4c$ of the tip part $4b$ of the suction nozzle 4 in the well plate 1B of this embodiment as in the well plate 1 of the second embodiment.

The grooves 13 are provided on the tapered part 11B. As shown in FIG. 6C, the grooves 13 are formed from the upper end part to the lower end part of the tapered part 11B and two grooves 13 are so provided that circumferential separation distances between the adjacent grooves 13 are substantially equal.

The number of the grooves 13 is not particularly limited and the well plate 1B of this embodiment may be formed with one groove 13 on the tapered part 11B or a plurality of grooves 13 on the tapered part 11B. When a plurality of grooves 13 are formed, the user can more stably position the suction nozzle 4 than when one groove 13 is formed. Further, since the plurality of grooves 13 can form more clearances S, a flow of liquid L is easily formed in sucking the subject 5 by the suction nozzle 4.

In the case of forming the plurality of grooves 13, the arrangement of the grooves 13 is not particularly limited. The well plate 1B of this embodiment can be so formed that the circumference distances between the adjacent grooves 13 are substantially equal or different in the case of forming the plurality of grooves 13 on the tapered part 11B.

In the case of forming the plurality of grooves 13 at equal intervals on the tapered part 11B, the arrangement of the clearances S formed by the respective grooves 13 and the suction nozzle 4 is uniform. Thus, the user can make liquid flows generated in the clearances S at the time of suction uniform. On the other hand, in the case of forming the grooves 13 such that the circumferential distances between adjacent grooves 13 are different, the sizes (widths) of the clearances S formed by the respective grooves 13 and the suction nozzle 4 are nonuniform. Thus, the user can change the liquid flows generated in the clearances S at the time of suction in a nonuniform manner. As a result, if the well plates 1B including the wells 3 formed with the grooves 13 in different arrangements are prepared, the user can select the well plate 1B capable of generating liquid flows, which make the suction of the subjects 5 easier, in accordance with the shapes of the subjects 5 desired to be held.

A width of the groove 13 is not particularly limited and may be such a width as to be able to form the clearance S capable of generating the liquid flow at the time of suction with the suction nozzle 4 inserted in the well 3B. For example, the width of the groove 13 is about ⅛ to ¼ of an outer circumferential length of the well 3B.

A depth of the groove 13 is not particularly limited and may be such a depth as to be able to form the clearance S capable of generating the liquid flow at the time of suction with the suction nozzle 4 inserted in the well 3B. For example, the depth of the groove 13 is about 80 to 800 µm.

The shape of the groove 13 is not particularly limited and various shapes including a V-shaped groove and a U-shaped groove can be adopted.

Figure 6D:
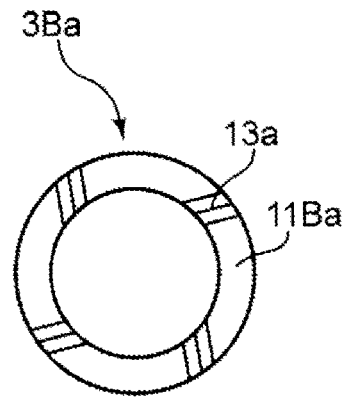

A method for forming the grooves 13 is not particularly limited and grooves (grooves 13$a$) may be obliquely formed on a tapered part 11Ba of a well 3Ba as shown in FIG. 6D. By obliquely forming the grooves, the user can generate a swirling liquid flow at the time of suction and efficiently collect the subject 5.

Note that disclosures having the following configurations are mainly included in the specific embodiments described above.

A well plate according to one aspect of the present disclosure is a well plate formed with a well for holding a subject to be sucked by a suction nozzle including a suction port on an inner bottom part and storing liquid, wherein a clearance forming member for forming a clearance to allow the liquid to flow in a state where a tip part of the suction nozzle including the suction port is inserted into and held in contact with the well is provided in the well.

According to the present disclosure, by adopting such a configuration, the clearance enabling the liquid to flow is formed near a contact position even in the state where the tip part of the suction nozzle including the suction port is inserted into and held in contact with the well in sucking the subject held in the well by the suction nozzle. In that state, the suction nozzle can suck the liquid around through the clearance formed by the clearance forming member. As a result, the subject held in the well is efficiently sucked through the suction port along the flow of the sucked liquid. Since a groove or the like is not formed on a cylindrical inner wall or the inner bottom part of the well, the subject is neither fitted into nor caught by a part of the well even if it has a soft property.

The well plate is preferably used by being immersed in a container storing liquid.

According to the present disclosure, by adopting such a configuration, a sufficient quantity of the liquid can be present in and around the well. Thus, the user can efficiently suck the subject held in the well.

Preferably, the well has a substantially cylindrical shape and the clearance forming member is a rib provided on an inner wall of the well.

According to the present disclosure, by adopting such a configuration, the rib can be brought into contact with a part of the suction nozzle to stably hold a suction position. Further, since the clearance is formed near the rib, the user can efficiently suck the subject by allowing the liquid to flow in sucking the subject.

Preferably, the rib is formed to extend upward from the inner bottom part of the well toward an opening and includes a sloped part on a part, and a projecting length of the sloped part from the inner wall of the well is longer near the inner bottom part than near the opening.

According to the present disclosure, by adopting such a configuration, the subject can be held in contact with the rib formed in the well. Since the sloped part is a downward inclined surface extending from the opening of the well toward the inner bottom part, the subject is easily introduced into the well and the flow of the liquid can be easily generated around the subject in sucking the subject by the suction nozzle.

A plurality of the ribs are preferably formed.

According to the present disclosure, by adopting such a configuration, the suction nozzle can be more stably positioned than when one rib is formed. Further, since the plurality of ribs can form more clearances, the flow of the liquid is easily formed in sucking the subject by the suction nozzle.

Preferably, the well has a substantially cylindrical shape and includes a tapered part for reducing an opening area of the well from an opening of the well toward the inner bottom part and the clearance forming member is a projection formed on the tapered part.

According to the present disclosure, by adopting such a configuration, the subject is easily introduced into the well via the tapered part downwardly inclined from the opening of the well toward the inner bottom part. Further, the suction nozzle can be positioned by bringing the tip part of the suction nozzle into contact with an inclined part of the tapered part.

A plurality of the projections are preferably formed.

According to the present disclosure, by adopting such a configuration, the plurality of projections can form more clearances than when one projection is formed. Thus, the flow of the liquid is easily formed in sucking the subject by the suction nozzle.

Preferably, the well has a substantially cylindrical shape and includes a tapered part for reducing an opening area of the well from an opening of the well toward the inner bottom part and the clearance forming member is a groove formed on the tapered part.

According to the present disclosure, by adopting such a configuration, the subject is easily introduced into the well via the tapered part downwardly inclined from the opening of the well toward the inner bottom part. Further, the suction nozzle can be positioned by bringing the tip part of the suction nozzle into contact with an inclined part of the tapered part.

A plurality of the grooves are preferably formed.

According to the present disclosure, by adopting such a configuration, the plurality of grooves can form more clearances than when one groove is formed. Thus, the flow of the liquid is easily formed in sucking the subject by the suction nozzle.

The wells are preferably formed in a matrix.

According to the present disclosure, by adopting such a configuration, a plurality of subjects can be simultaneously arranged, which can contribute to operation efficiency.

The subject is preferably a bio-based cell.

According to the present disclosure, by adopting such a configuration, a contribution can be made to operation efficiency in the fields of bio-related technology and medicine since the well plate can be applied for bio-based cells which are subjects with large shape deviations.

The subject is preferably a bio-based cell aggregate.

According to the present disclosure, by adopting such a configuration, a test result considering functions of individual cells can be obtained as compared with a test result obtained using one cell since a biosimilar environment considering interactions among cells is reconfigured in the cell aggregate, and experiment conditions can be made uniform in accordance with an environment in a biological body. Thus, the well plate can provide a highly reliable result in the fields of bio-related technology and medicine.

A suction device according to another aspect of the present disclosure includes a well plate formed with a well for holding a subject on an inner bottom part and storing liquid, and a suction nozzle including a suction port for sucking the subject held in the well, wherein the well includes a clearance forming member for forming a clearance to allow the liquid to flow in a state where a tip part of the suction nozzle including the suction port is inserted into and held in contact with the well.

According to the present disclosure, by adopting such a configuration, the clearance enabling the liquid to flow is formed near a contact position even in the state where the tip part of the suction nozzle including the suction port is inserted into and held in contact with the well in sucking the subject held in the well by the suction nozzle. In that state, the suction nozzle can suck the liquid around through the clearance formed by the clearance forming member. As a result, the subject held in the well is efficiently sucked through the suction port along the flow of the sucked liquid. Since a groove or the like is not formed in the well, the subject is neither fitted into nor caught by a part of the well even if it has a soft property.

Preferably, the suction device further includes a container for storing liquid and the well plate is immersed in the container.

According to the present disclosure, by adopting such a configuration, a sufficient quantity of the liquid can be present in and around the well. Thus, the user can efficiently suck the subject held in the well.

It is preferable to further include a vibration generating device for vibrating the well plate in a state where the tip part of the suction nozzle including the suction port is inserted into and held in contact with the well.

According to the present disclosure, by adopting such a configuration, the subject held in the well can be caused to temporarily float. As a result, the subject is easily sucked by the suction nozzle, which contributes to operation efficiency.

It is preferable to further include a determining device for observing the subject held in the well plate from above or below the well plate.

According to the present disclosure, by adopting such a configuration, whether or not the subject is held in the well plate can be determined. Further, the positions of the suction port of the suction nozzle and the opening of the well can be easily confirmed. Furthermore, since the user can confirm the shape of the subject held in the well before suction by the determining device, the subject, which is not supposed to be sucked due to a distorted shape or the like, can be eliminated from suction targets if such a subject is held in the well.

The invention claimed is:

1. A well plate comprising
a well for holding a subject to be sucked by a suction nozzle including a suction port on an inner bottom part and storing liquid,
a clearance forming member for forming a clearance to allow liquid to flow in a state where a tip part of the suction nozzle including the suction port is inserted into and held in contact with the well is provided in the well;
the well having a cylindrical shape and including a tapered part for reducing an opening area of the well from an opening of a top surface of the well toward the inner bottom part; the tapered part being a wall having no openings, and the clearance forming member being at least one groove formed on the tapered part.

2. The well plate according to claim 1, wherein there are a plurality of grooves formed on the tapered part.

3. The well plate according to claim 1, wherein a plurality of the wells are formed in a matrix.

4. The well plate according to claim 1, wherein the subject is a bio-based cell.

5. The well plate according to claim 4, wherein the subject is a bio-based cell aggregate.

6. A suction device, comprising:
a well plate according to claim 1, and
a suction nozzle including a suction port for sucking the subject held in the well.

7. The suction device according to claim 6, further comprising a container for storing the liquid, wherein the well plate is immersed in the container.

8. The suction device according to claim 6, further comprising a vibration generator device for vibrating the well plate in a state where the tip part of the suction nozzle including the suction port is inserted into and held in contact with the well.

9. The suction device according to claim 7, further comprising a determiner device for observing the subject held in the well plate from above or below the well plate.

* * * * *